United States Patent [19]

Saitoh

[11] Patent Number: 5,163,446
[45] Date of Patent: Nov. 17, 1992

[54] ELECTROMAGNETIC HEATING DEVICE

[75] Inventor: Yoshiaki Saitoh, Niigata, Japan

[73] Assignee: Omron Corporation, Nagaokakyo, Japan

[21] Appl. No.: 568,141

[22] Filed: Aug. 16, 1990

Related U.S. Application Data

[63] Continuation of Ser. No. 480,482, Feb. 16, 1990, abandoned.

[30] Foreign Application Priority Data

Feb. 16, 1989 [JP] Japan ................................ 1-36600
Feb. 16, 1989 [JP] Japan ................................ 1-36601

[51] Int. Cl.⁵ .............................................. A61N 5/00
[52] U.S. Cl. .................................... 128/804; 128/402
[58] Field of Search ................................ 128/804, 402; 219/10.55 F, 10.55 R

[56] References Cited

U.S. PATENT DOCUMENTS

| | | | |
|---|---|---|---|
| 4,028,518 | 6/1977 | Boudouris et al. | 128/804 X |
| 4,660,572 | 4/1987 | Maruyama et al. | |

FOREIGN PATENT DOCUMENTS

| | | | |
|---|---|---|---|
| 216665 | 1/1961 | Austria | 128/804 |
| 0034735 | 9/1981 | European Pat. Off. | |
| 2420883 | 11/1975 | Fed. Rep. of Germany | |
| 8907469 | 8/1989 | World Int. Prop. O. | 128/804 |

OTHER PUBLICATIONS

Saitoh et al, "Resonant Cavity Applicator . . . ", Proc. Symp. on Hyperthermic Oncology, vol. 1, 1989, pp. 837–838.

*Primary Examiner*—Lee S. Cohen
*Attorney, Agent, or Firm*—Fish & Richardson

[57] ABSTRACT

An electromagnetic heating device for heating a living body or an object, comprising a cavity resonator made of hollow electroconductive material for receiving a living body or an object therein and heating same by a high frequency electromagnetic field produced therein; and at least an electric field concentrator disposed in the cavity resonator separately therefrom. Thus, it is possible to concentrate an electric field to a desired location to supply a strong current into a living body or an object. Further, since the electric field concentrator is electrically out of contact with the cavity resonator, a frequency adjusting element and an impedance matching element may be easily provided in the vicinity for optimum transmission of high frequency electromagnetic energy thereby eliminating the need for adjusting the frequency of the high frequency electromagnetic energy source. Since an oscillator without the capability to change its frequency can be manufactured at a fraction of the cost for manufacturing a variable frequency oscillator, the cost of the overall heating device can be drastically reduced. By shaping the free end of the electric field concentrator, it is possible to achieve a desired degree of energy concentration.

20 Claims, 12 Drawing Sheets

ELECTROMAGNETIC HEATING DEVICE

This is a continuation of application Ser. No. 07/480,482 filed on Feb. 16, 1990, abandoned.

TECHNICAL FIELD

The present invention relates to an electromagnetic heating device using a cavity resonator for heating a living body or an object, and in particular to an electromagnetic heating device which may be advantageously used for heating a living object, for instance for the treatment of cancer and other ailments.

BACKGROUND OF THE INVENTION

Cavity resonators, have been conventionally used in electromagnetic heaters for heating living bodies and objects. According to a typical electromagnetic heating device, as shown in FIGS. 33(A) and 33(B), a pair of projections (reentrants) 4a and 4b are integrally provided in the upper and lower internal walls 2a and 2b of a cavity resonator 1 consisting of a cylindrical metallic conductor, and a pair of openings 3a and 3b are provided in its side wall 6 to introduce a living body 5 or an object thereinto. High frequency electromagnetic energy is supplied to the cavity resonator 1 from outside.

In such an electromagnetic heating device, it is desired to be able to concentrate high frequency electromagnetic energy to a desired spot at a high efficiency. However, it is known that when the size of the object 5 to be heated changes, the resonant frequency of the cavity resonator changes to such an extent that an efficient electromagnetic heating effect cannot be attained. Therefore, it was necessary to change the frequency of the oscillator for supplying high frequency energy according to the size of the object in order to achieve an appropriate heating. However, when the oscillation frequency of a high frequency oscillator is to be made variable, the ocisllator becomes accordingly more complex, and combined with the need to achieve an impedance matching anew every time a change in the frequency occurs the device would be even more complex and expensive.

It is conceivable to provide a link coil as means for adjusting the resonant frequency of the cavity resonator and achieving an efficient transmission of high frequency energy into the cavity resonator. However, the use of a link coil does not necessarily ensure an efficient supply of high frequency energy cavity resonator produces a change in the impedance of the cavity resonator as seen from the high frequency electromagnetic energy source.

Further, it is known that the point of concentration of electric current is difficult to keep fixed, and that it tends to shift according to the shape and electric constants of the object to be heated. For this reason, it has been impossible to keep a location to be heated at a high temperature all the time. It has therefore been desired to be able to concentrate high frequency energy to a highly localized region of the object to be heated irrespective of the conditions of the object to be heated.

BRIEF SUMMARY OF THE INVENTION

In view of such problems of the related art, a primary object of the present invention is to provide an electromagnetic heating device using a cavity resonator which can transmit high frequency electromagnetic energy to an object to be heated at a high efficiency even when the conditions of the object has changed, and can thereby ensure an efficient transmission of electromagnetic energy to the object.

A second object of the present invention is to provide an electromagnetic heating device which can concentrate electromagnetic energy to a small region inside the object to be heated.

A third object of the present invention is to provide an electromagnetic heating device which can heat an internal part of an object without excessively raising its surface temperature.

A fourth object of the present invention is to provide an electromagnetic heating device which is simple in structure yet is capable of transmitting high frequency energy to an object to be heated at high efficiency irrespective of the conditions of the object to be heated.

These and other objects of the present invention can be accomplished by providing an electromagnetic heating device for heating a living body or an object, comprising a cavity resonator made of hollow electroconductive material for receiving a living body or an object therein and heating same by a high frequency electromagnetic field produced therein; and at least an electric field concentrator disposed in the cavity resonator separately therefrom.

Thus, according to a broad concept of the present invention, it is possible to concentrate an electric field by placing an electric field concentrator made of a conductor adjacent to a location to be heated because a conductor more readily conducts electric current than air and can therefore concentrate the electric field to a desired location to supply a strong current into a living body or an object. Further, since the electric field concentrator may be electrically out of contact with the cavity resonator, frequency adjusting means for changing the resonant frequency of the cavity resonator can be easily provided in the vicinity. If the electric field concentrator comprises a tubular body having a projection at its fee end, it is possible to localize the electric field to an extremely small region. Typically, the electric field concentrator comprises a pair of electric concentrating members spaced from each other to define a space for accommodating a living body or an object to be heated therebetween.

According to a preferred embodiment of the present invention, the frequency adjusting means may comprise a variable capacitor connected between a wall portion of the cavity resonator and the electric field concentrator. Alternatively, the frequency adjusting means may comprise means for deforming the electric field concentrator, means for varying a position of the electric field concentrator relative to the cavity resonator, a variable inductance element connected between the electric field concentrator and a wall portion of the cavity resonator, an enclosed container interposed between the electric field concentrator and a wall portion of the cavity resonator combined with means for changing a medium filled in the electric field concentrator, or an enclosed container interposed between the electric field and a wall portion of the cavity resonator combined with means for changing a volume of the container by changing a pressure of a medium filled in the electric field concentrator. In the last mentioned case, the container may be integral with the electric field concentrator. In either case, there is no need to change the oscillating frequency of the high frequency signal source.

According to another broad concept of the present invention, there is provided an electromagnetic heating device for heating a living body or an object, comprising: a cavity resonator made of hollow electroconductive material for receiving a living body or an object therein and heating same by a high frequency electromagnetic field produced therein; a link coil connected to an input end of the cavity resonator; and impedance matching means provided adjacent to the link coil.

According to this aspect of the present invention, high frequency energy is supplied from the link coil to the cavity resonator via the impedance matching means. In this way, an impedance matching is taken by the impedance matching means between the impedance of the link coil and the impedance of the feeder cable of the high frequency power source, and high frequency energy can be supplied in a smooth and efficient manner. Since the impedance matching means is provided adjacent to the link coil either inside or outside the cavity resonator, adjustment of impedance matching can be carried out readily and easily.

According to a certain aspect of the present invention, the electromagnetic heating device comprises a high frequency power source; a cavity resonator made of hollow electroconductive material for receiving a living body or an object therein and heating same by a high frequency electromagnetic field produced therein; at least one electric field concentrator disposed in the cavity resonator; high frequency energy input means for supplying high frequency energy from the high frequency power source into the cavity resonator; frequency adjusting means for adjusting a resonant frequency of the cavity resonator; a pick-up coil for picking up a signal in the cavity resonator; a resonant condition detecting means for detecting a signal output from the pick-up coil; and control means for controlling the frequency adjusting means according outputs from the resonant condition detecting means. Preferably, there are further provided impedance matching condition detecting means and impedance matching condition adjusting means, and the control means controls both the frequency adjusting means and the impedance matching condition adjusting means according to outputs form the resonant condition detecting means and the impedance matching condition detecting means.

According to this electromagnetic heating device, high frequency energy from the high frequency power source is supplied by the input means to the cavity resonator. A signal from the cavity resonator is picked up by the pick-up coil such as a link coil while heating the living body or the object, and its output voltage is detected by the resonant condition detector so that the control means may control the frequency adjusting means and the impedance matching condition adjusting means according to the detected output or the detected resonant condition and the impedance matching condition. The resonant frequency of the cavity resonator is adjusted so as to maximize the output of the resonant detector.

BRIEF DESCRIPTION OF THE DRAWINGS

Now the present invention is described in the following in more detail in terms of specific embodiments with reference to the appended drawings, in which.

DESCRIPTION OF THE PREFERRED EMBODIMENTS

Figure 1A:
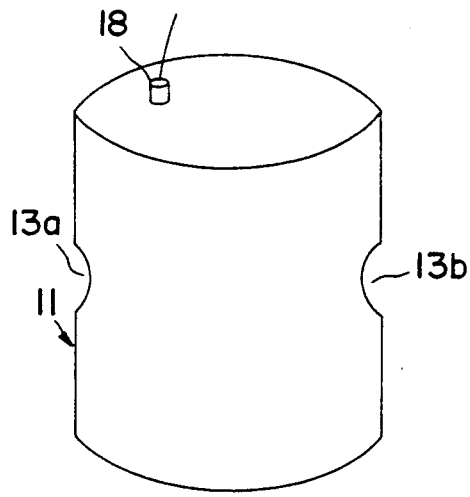
FIG. 1(A) is an external perspective view of an embodiment of the electromagnetic heating device according to the present invention.
Figure 1B:
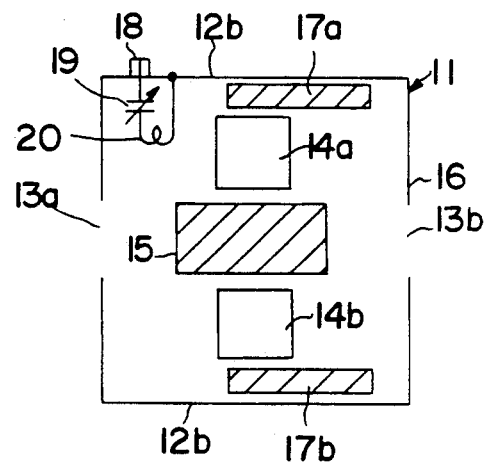
FIG. 1(B) is a longitudinal sectional view of the electromagnetic heating device.
Figure 33A:
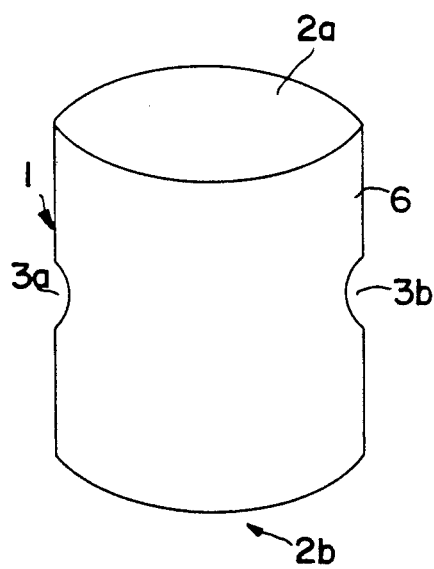
FIG. 33(A) is an external perspective view of a conventional electromagnetic heating device.
Figure 33B:
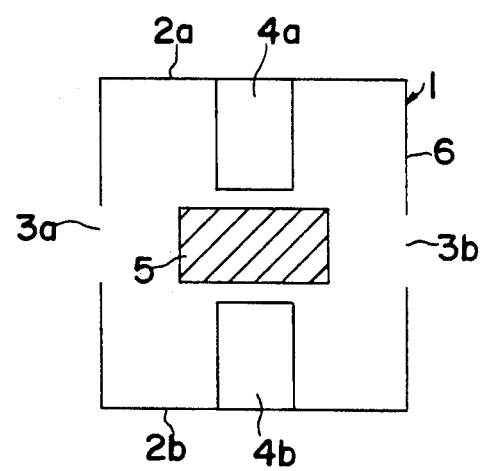
FIG. 33(B) is a longitudinal sectional view of the conventional electromagnetic heating device.

FIG. 1(A) is a perspective external view of a cavity resonator 11 of an electromagnetic heating device constructed as an embodiment of the present invention, and FIG. 1(B) is a longitudinal sectional view of the cavity resonator 11. Referring to these drawings, the cavity resonator 11 is a cylindrical body made of a metallic conductor, and is provided with openings 13a and 13b in its side wall 16 to introduce a living body or an object 15 thereinto. Further, the cavity resonator 11 is internally provided with electric field concentrators 14a and 14b. These electric field concentrators 14a and 14b are not exactly integral with upper and lower walls 12a and 12b of the cavity resonator 11, but supported thereby by way of support means (now shown in the drawings) so as to be electrically separated from each other. A pair of frequency adjustors 17a and 17b are provided between the upper and lower walls 12a and 12b of the cavity resonator 11 and the associated electric field concentrators 14a and 14b, respectively, so that the frequency of the cavity resonator 11 may be adjusted by changing their thicknesses and relative dielectric constants. If the resonant frequency is too high, it may be lowered by increasing the thicknesses of the frequency adjustors 17a and 17b and/or by using a material having a large relative dielectric constant for the frequency adjustors 17a and 17b. Conversely, if the resonant frequency is too low, the thicknesses of the frequency adjustors 17a and 17b may be reduced or a material having a lower relative dielectric constant may be used.

The upper wall 12a of the cavity resonator 11 is externally provided with a connector 18, and is internally provided with a link coil 20, adjacent to the electric field concentrator 14a, which is connected to the upper wall 12a at its one end and to a signal terminal of the connector 18 via a variable capacitor 19 at its other end. The variable capacitor 19 serves as a capacitor (impedance matching element) for impedance matching.

When a feeder cable leading to a high frequency power source is connected to the connector 18 of this electromagnetic heating device to supply high frequency energy to the cavity resonator 11 via the connector 18, the variable capacitor 19 and the link coil 20, and a living body or an object 15 is placed between the electric field concentrators 14a and 14b, the living body or the object 15 is heated. It is possible to supply high frequency energy merely by connecting the link coil 20 to the connector 18, but connecting this link coil 20 to the connector 18 along may not ensure an efficient transmission of high frequency energy due to mismatching of impedance between the link coil 20 and the feeder cable. Therefore, according to the present embodiment, the variable capacitor 19 is connected between the connector 18 and the link coil 20 as an impedance matching element. Therefore, according to this embodiment, the variable capacitor 19 is connected between the connector 18 and the link coil 20. The variable capacitor 19 is disposed adjacent to the upper wall in the cavity resonator 11 in this embodiment, but it may also be placed on the upper wall outside the cavity resonator 11.

Figure 2:
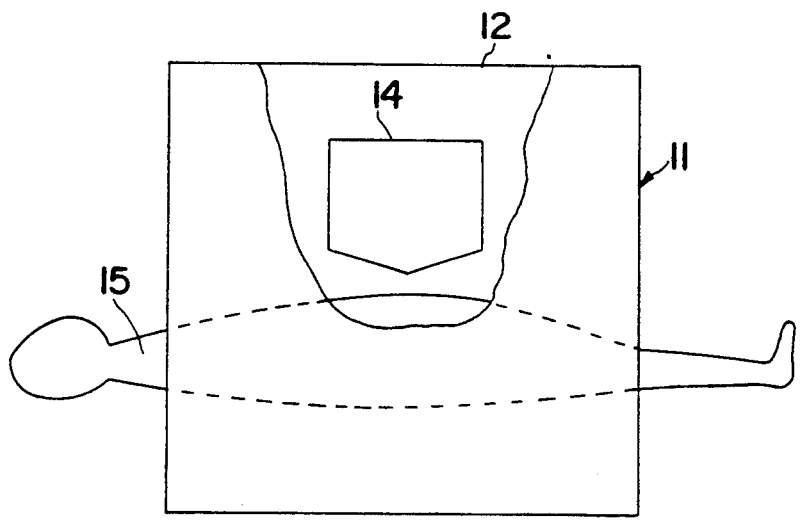
FIG. 2 is a schematic view showing an embodiment of the present invention.
Figure 3:
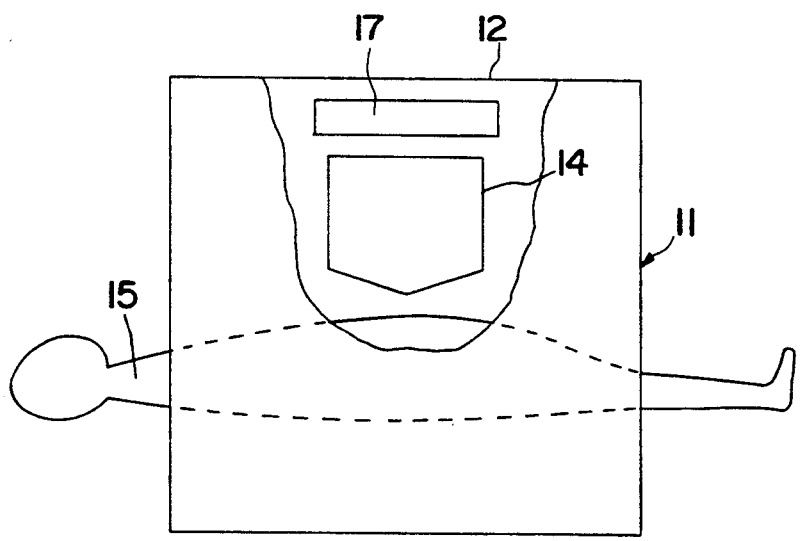
FIG. 3 is a schematic view showing another embodiment of the present invention.
Figure 4:
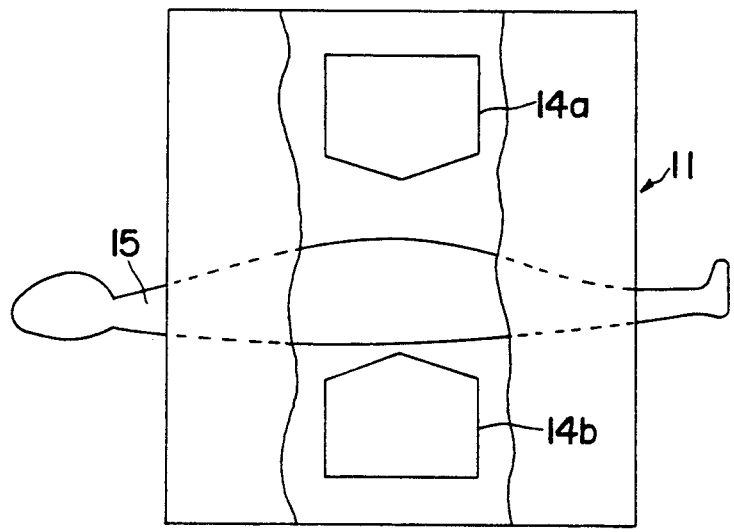
FIG. 4 is a schematic view showing yet another embodiment of the present invention.

In the above described embodiment, the cavity resonator 11 was provided with a pair of electric field concentrators 14a and 14b and is constructed as a cylindrical body so that a living body 15 may be placed in the space defined between the electric field concentrators 14a and 14b. However, the cavity resonator of the present invention is not limited to a cylindrical shape, but may also have rectangular and other shapes. It may be provided with at least one electric field concentrator 14 as illustrated in FIG. 2, may comprise a frequency adjustor 17 between the electric field concentrator 14 and a bottom wall of the cavity resonator 11 as shown in FIG. 3, or may comprise a pair of electric field concentrators 14a and 14b to place a living body or an object to be heated therebetween as illustrated in FIG. 4.

Figure 6A:
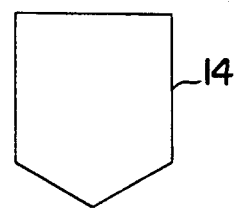
FIGS. 6(A), 7(A) and 8(A) are schematic side views of electric field concentrators.
Figure 7A:
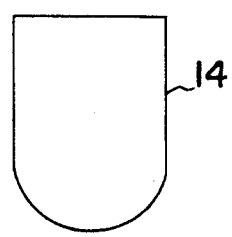
Figure 8A:
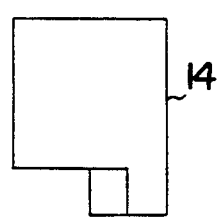
Figure 6B:
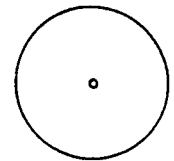
FIGS. 6(B), 7(B) and 8(B) are schematic bottom views of the electric field concentrators.
Figure 7B:
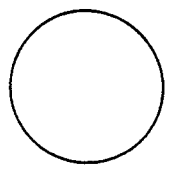
Figure 8B:
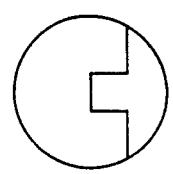

Also, the free end of the electric field concentrator 14 may be sharply tapered as shown in FIGS. 6(A) and 6(B), rounded to a spherical shape as shown in FIGS. 7(A) and 7(B), or shaped into a special shape which corresponds to a desired heating pattern as shown in FIGS. 8(A) and 8(B).

Figure 5:
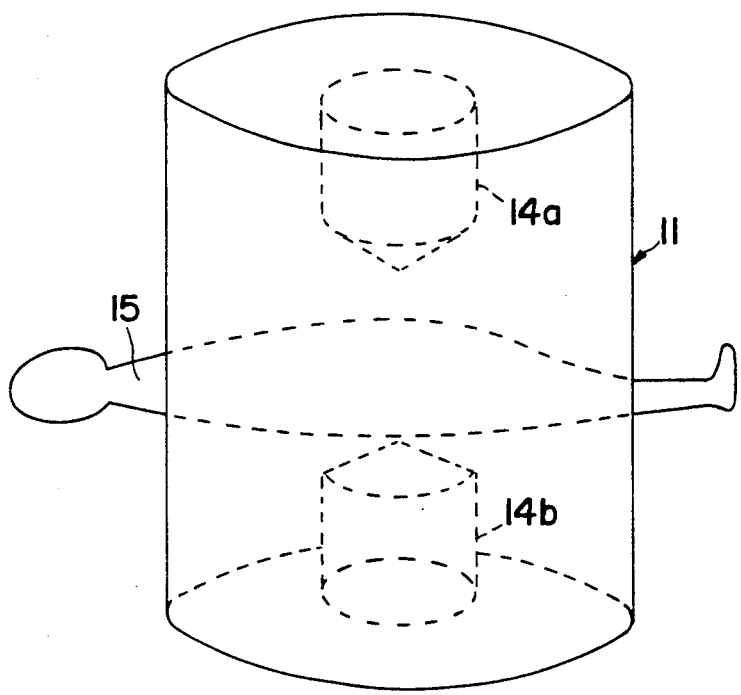
FIG. 5 is a schematic view illustrating an essential part of FIGS. 1(A) and 1(B)

Since electric current is injected from the free end of the electric field concentrator 14, it is possible to heat an extremely narrow region by using the pointed shape at the free end of the electric field concentrator 14 as illustrated in FIGS. 5, 6(A) and 6(B). When the free end is spherical as illustrated in FIGS. 7(A) and 7(B), a slightly wider region is heated. When the free end is flat, an even wider heating region can be obtained. By thus appropriately selecting the shape of the free end of the electric field concentrator 14, it becomes possible to control not only the location to be heated but also the shape of the region to be heated so that a high therapeutic effect can be obtained in treating cancer by heating only the cancerous portion according to its shape.

Possibility of adjusting the resonant frequency by changing the thicknesses and the relative dielectric constants of the frequency adjustors 17a and 17b was discussed by referring to FIG. 1. In the following, various other examples of frequency adjustors are described.

Figure 9:
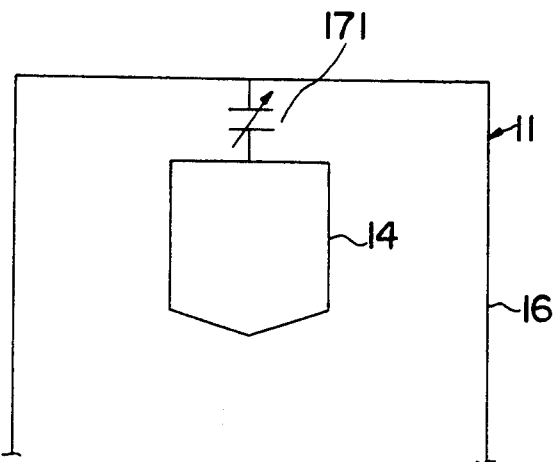

Referring to FIG. 9, a variable capacitor 171 is provided between an upper end wall 12a of the cavity resonator 11 and the electric field concentrator 14. This variable capacitor 171 may also be connected between a side wall 16 of the cavity resonator 11 and the electric field concentrator 14. If desired, it may be in contact with the living body or the object 15 and the electric field concentrator 14. The variable capacitor 171 may preferably consist of a rotary variable capacitor which changes its capacitance as its polar plates are turned. When such a variable capacitor is connected between an end walls 12a or 12b, or a side wall 16 and the electric field concentrator, it can function as a frequency adjustor and can adjust the resonant frequency.

By providing both the frequency adjustor 17 illustrated in FIG. 1 and the variable capacitor 171 described here, it is possible to roughly set up a resonant frequency with the frequency adjustor 17 and finely tune it with the variable capacitor 171.

According to this embodiment, the resonant frequency of the cavity resonator can be fixed to a constant value. Further, an extremely accurate frequency tuning is possible by changing the rotational angle of the variable capacitor 171 very little by little. Therefore, the frequency of the oscillator for supplying high frequency electric power may be fixed, and is not required to be variable. Since an oscillator without the capability to change its frequency can be manufactured at a fraction of the cost for manufacturing a variable frequency oscillator, the cost of the overall heating device can be drastically reduced.

Figure 10:
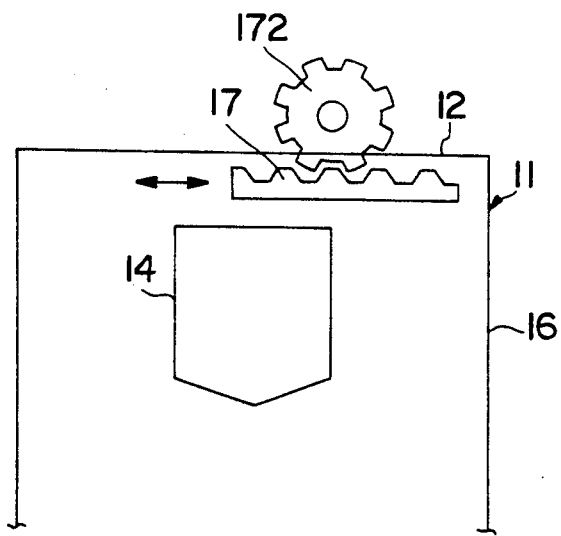

FIG. 10 shows a structure in which the relative position between the electric field concentrator 14 and the frequency adjustor 17 can be varied. The frequency adjustor 17 is provided with a rack which may be driven by a gear 172 so that the frequency adjustor 17 may be moved by rotating the gear 172 mounted on the bottom wall 12.

Figure 11:
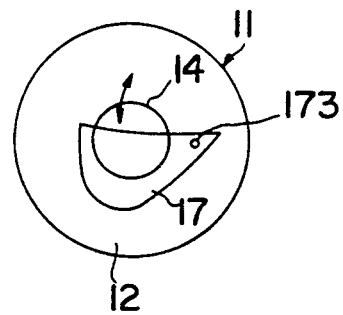

FIG. 11 shows a structure in which the frequency adjustor 17 is provided with the shape of a fan, and the base end of this fan shape 173 is pivotably secured in a rotatable fashion so that the free end of the frequency adjustor 17 may be rotated.

According to the structures illustrated in FIGS. 10 and 11, the relative position between the electric field concentrator 14 and the frequency adjustor 17 can be changed, and the areas of their mutually opposing surfaces can be changed. As a result, the resonant frequency of the overall cavity resonator 11 can be changed. When the resonant frequency is too high, the areas of the opposing surfaces may be increased to thereby lower the resonant frequency. Conversely, when the resonant frequency is too low, the areas of the mutually opposing surfaces may be reduced to thereby raise the resonant frequency. Thus, it is possible to achieve a fixed resonant frequency by appropriately moving the frequency adjustor according to the size of the living body or the object received therein. Since an oscillator without the capability to change its frequency can be manufactured at a fraction of the cost for manufacturing a variable frequency oscillator, the cost of the overall heating device can be drastically reduced.

Figure 12:
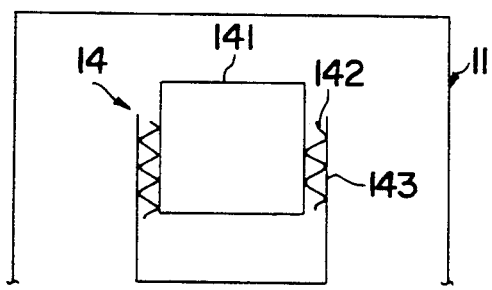

According to the structure illustrated in FIG. 12, the electric field concentrator 14 is made up of a pair of conductive cylinders 141 and 143, and a metallic spring 142 interposed between the inner conductive cylinder 141 and the outer conductive cylinder 143 so as to ensure a favorable electric conduction therebetween. The electric field concentrators 141 and 143 can be moved and deformed. Their overall volume may be changed simply by pulling or pushing the conductive cylinder 143 of the electric field concentrator 14 relative to the other conductive cylinder 141 by hand or by some other means. The electric field concentrator 14 is accommodated in the cavity resonator 11, and occupies a part of its internal space. By increasing this occupied space, the resonant frequency of the cavity resonator may be lowered. Conversely, by reducing the occupied space, the resonant frequency may be raised. Therefore, according to this embodiment, the resonant frequency of the cavity resonator 11 can be lowered by increasing the overall volume of the conductive cylinders 141 and 143 of the electric field concentrator 14 by stretching the conductive cylinders 141 and 143, and this process may also be reversed. In short, the resonant frequency of the cavity resonator can be adjusted.

Figure 13:
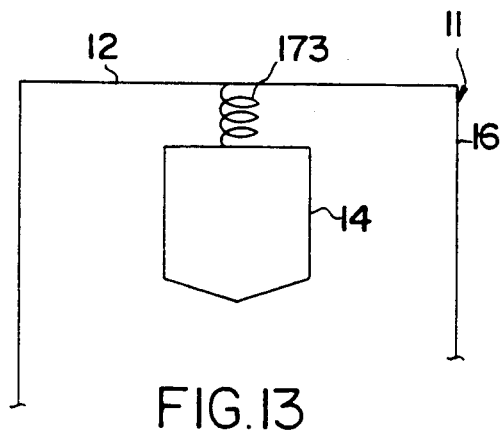
Figure 14:
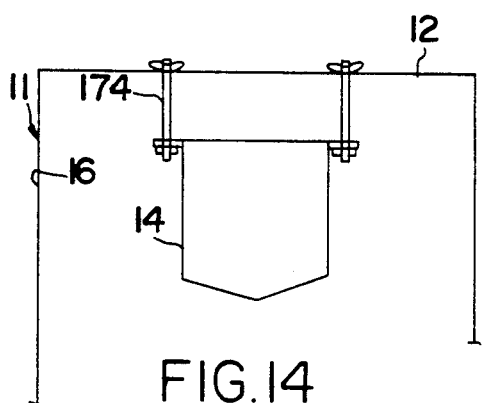

According to the structure illustrated in FIG. 13, the bottom wall 12 or the side wall 16 of the cavity resonator 11 and the electric field concentrator 14 are connected to each other by a coil 173. According to the structure illustrated in FIG. 14, the bottom wall 12 of the cavity resonator 11 and the electric field concentrator 14 are connected to each other by a conductive rod 174.

The resonant frequency of a cavity resonator may be lowered by inserting the coil 173 between the wall surface of the cavity resonator and the electric field concentrator 14. By changing the shape of this coil and thereby changing its inductance, the resonant frequency of the cavity resonator can be changed. By shrinking the coil, its inductance is increased, and the resonant frequency of the cavity resonator is lowered. Conversely, by extending the coil, the resonant frequency may be raised. In a high frequency range, an inductance is produced even when conductive wires or conductive rods are used instead of a coil, and the resonant frequency may be adjusted according to the thickness of the conductive wires or the conductive rods and their number. For instance, as the thickness is increased or the number of the used conductors increases, the inductance diminishes, and the resonant frequency rises. Further, by adding a frequency adjustor 17 made of a dielectric material and/or a variable capacitor 171, the resonant frequency may be further adjusted.

According to these embodiments, the resonant frequency of the cavity resonator 11 can be lowered by adding a coil, and a low resonant frequency can be achieved while keeping the diameter of the cavity resonator the same. Generally speaking, an oscillator for a lower frequency is more economical, and this method allows the device to be manufactured economically.

FIGS. 15 through 19 show yet other embodiments of the frequency adjusting means. These frequency adjusting means are all based on changing of the volume of the cavity resonator.

Figure 15:
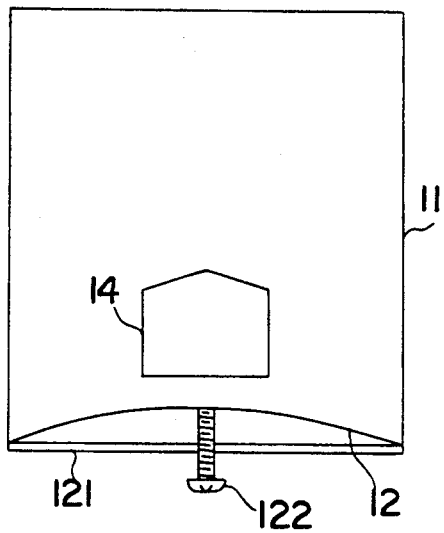

In the embodiment illustrated in FIG. 15, a beam 121 is provided on the outer surface of the bottom wall 12 of the cavity resonator 11, and a screw 122 is mounted on this beam 121 so that the bottom wall 12 may be pushed inwards and outwards by turning the screw 122. When the bottom wall 12 has an outwardly bulging out shape, the beam 121 should then be provided with an outwardly bulging out shape accordingly. The screw 122 may be turned either manually or by an electric motor.

Figure 16:
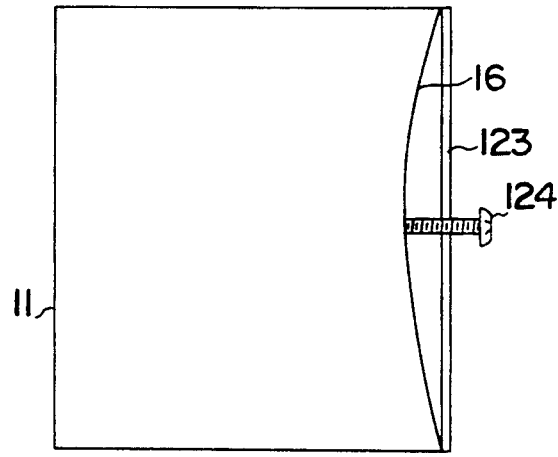

According to the embodiment illustrated in FIG. 16, a beam 123 is provided on the outside of a side wall of a cavity resonator 11 so that the wall surface 16 may be deformed either convex or concave by turning the screw 124.

Figure 17:
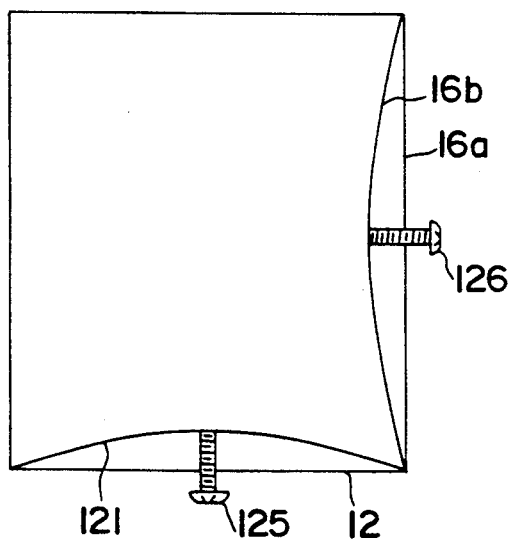

According to the embodiment illustrated in FIG. 17, a second wall surface 121 or 16b is provided inside the bottom wall 12 or the side wall 16a of the cavity resonator, and screws 125 and 126 are provided in the walls 12 and 16a so that the inner wall surfaces 121 and 16b may be changed by adjusting these screws 125 and 126.

Figure 18:
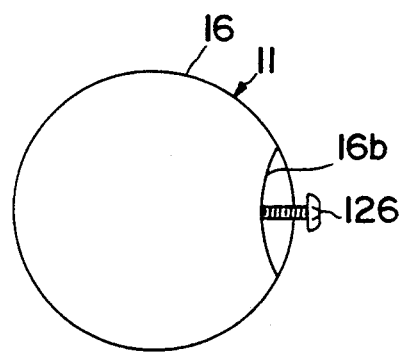
Figure 19:
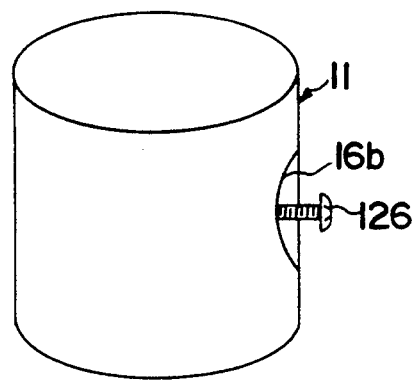

In the case of the embodiment illustrated in FIG. 18, a double inner wall 16b is provided vertically along a part of the side wall 16 of the cavity resonator 11, and in the case of the embodiment illustrated in FIG. 19 an inner wall 16b is internally and locally provided along a circumferential direction and a vertical direction.

In the case of the cavity resonator illustrated in FIGS. 15 through 19, the internal volume of the cavity resonator 11 may be adjusted by using a screw to the end of varying its resonant frequency. When the volume of the cavity resonator is increased, the resonant frequency of the cavity resonator becomes lower.

Figure 21:
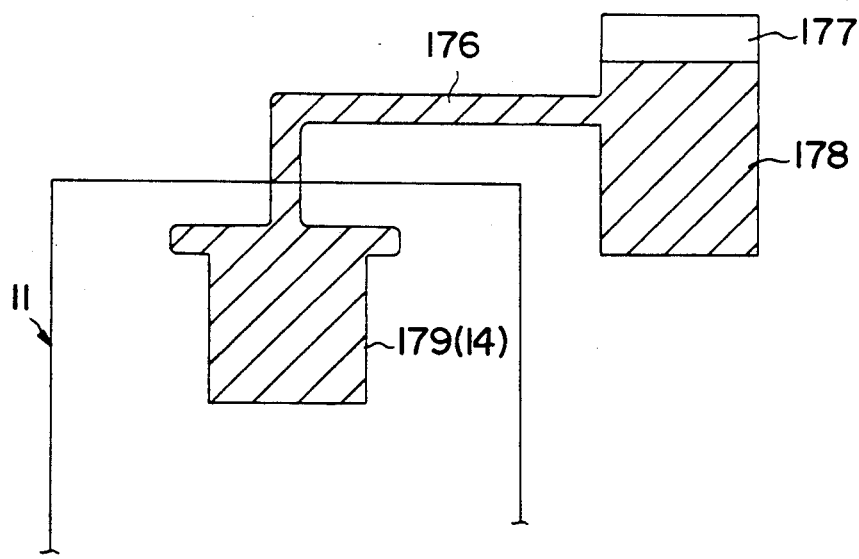
FIG. 9, FIG. 10, FIG. 11, FIG. 12, FIG. 13, FIG. 14, FIG. 15, FIG. 16, FIG. 17, FIG. 18, FIG. 19, FIG. 20, and FIG. 21 are views showing different embodiments of the frequency adjusting means.
Figure 20:
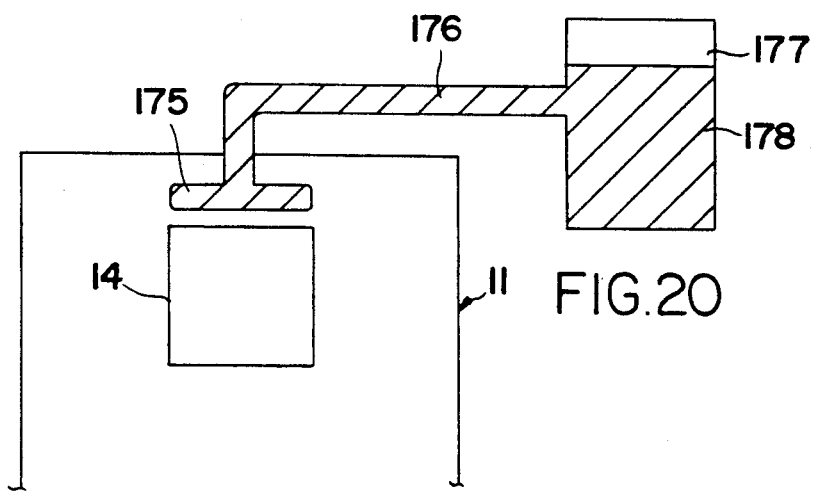

FIGS. 20 and 21 are views showing yet other embodiments of the frequency adjusting means. In the case of the embodiment illustrated in FIG. 20, the frequency adjustor 175 is enclosed, and the volume and the kind of the fluid 178 filled thereinto can be adjusted. To adjust the volume of the fluid, a siphon may be used to introduce the fluid from a reservoir 177 via a pipe 176. The kind of the fluid may be selected from those involving a little electric loss, and having a different relative dielectric constant. The material for the frequency adjustor 175 may consist of a soft material so as to induce a change in the shape of the frequency adjustor 175.

According to this embodiment, when the volume of the frequency adjustor 175 is large, the resonant frequency of the cavity resonator 11 is low. Further, for a given volume, the larger the relative dielectric constant of the dielectric material existing in the frequency adjustor 175 is, the lower the resonant frequency of the cavity resonator 11 becomes. The converse is also true. Thus, the resonant frequency of the cavity resonator 11 can be adjusted. Further, even when the external shape of the frequency adjustor 175 is fixed, it is still possible to adjust the resonant frequency according to the amount of the dielectric material existing therein.

In the case of the embodiment illustrated in FIG. 21, the electric field concentrator 14 is made of dielectric material, and the frequency adjustor 175 of FIG. 20 is modified into an integral frequency adjustor 179. By this means also, the frequency may be adjusted. The functions thereof are substantially the same as those of the embodiment illustrated in FIG. 20.

Figure 22:
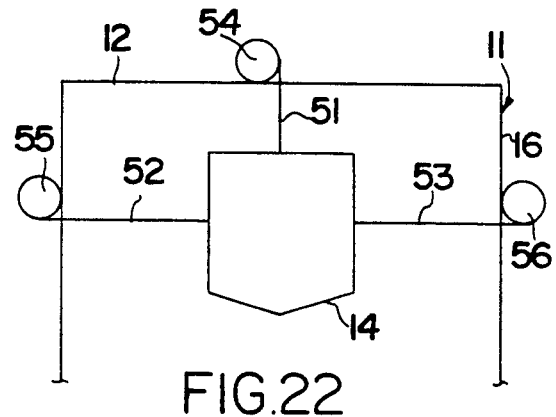
FIG. 22 is a view showing a mechanism for moving the electric field concentrator.

FIG. 22 shows an example of a mode of supporting the electric field concentrator 14. The electric field concentrator 14 is supported by a bottom wall 12 and side walls 16 by way of wires 51, 52 and 53 made of dielectric material. The electric field concentrator 14 may be moved vertically and laterally by pulling and paying out these wires 51, 52 and 53 by pulleys or electric motors 54, 55 and 56. It is also possible to move the electric field concentrator 14 by securing the electric field concentrator 14 with a dielectric rod instead of the wires 51, 52 and 53, and moving this dielectric rod vertical and laterally.

It is also possible to construct the electric field concentrator out of two or more parts each of which is partially secured and allowed to move only at its free end.

By changing the position of the electric field concentrator, it is possible to change the pattern of the electric current injected from the free end thereof. Therefore, when the location to be heated is desired to be changed only slightly, it can be accomplished without moving the living body or the object. If there is any inconvenience in changing the resonant frequency and/or the impedance by moving the electric field concentrator, the position to be heated can be changed without substantially affecting the resonant frequency and the impedance by constructing the electric field concentrator from two or more parts which are partially secured so as to permit the movement of their free ends.

According to this embodiment, an accurate positioning of the part to be heated is possible, and a high therapeutic effect may be achieved in case of heating a living body. When a living body is to be interposed between a pair of moveable electric field concentrators (which may be moveable only at their free ends), even when the electric field concentrators are moved, a desired position to be heated deep inside the living body can be always heated and the deep body part can be heated to a high temperature as long as the electric field concentrators are moved appropriately in different directions while the electric current flow pattern on the body surface keeps changing and prevents any excessive rise in the surface temperature.

Figure 23:
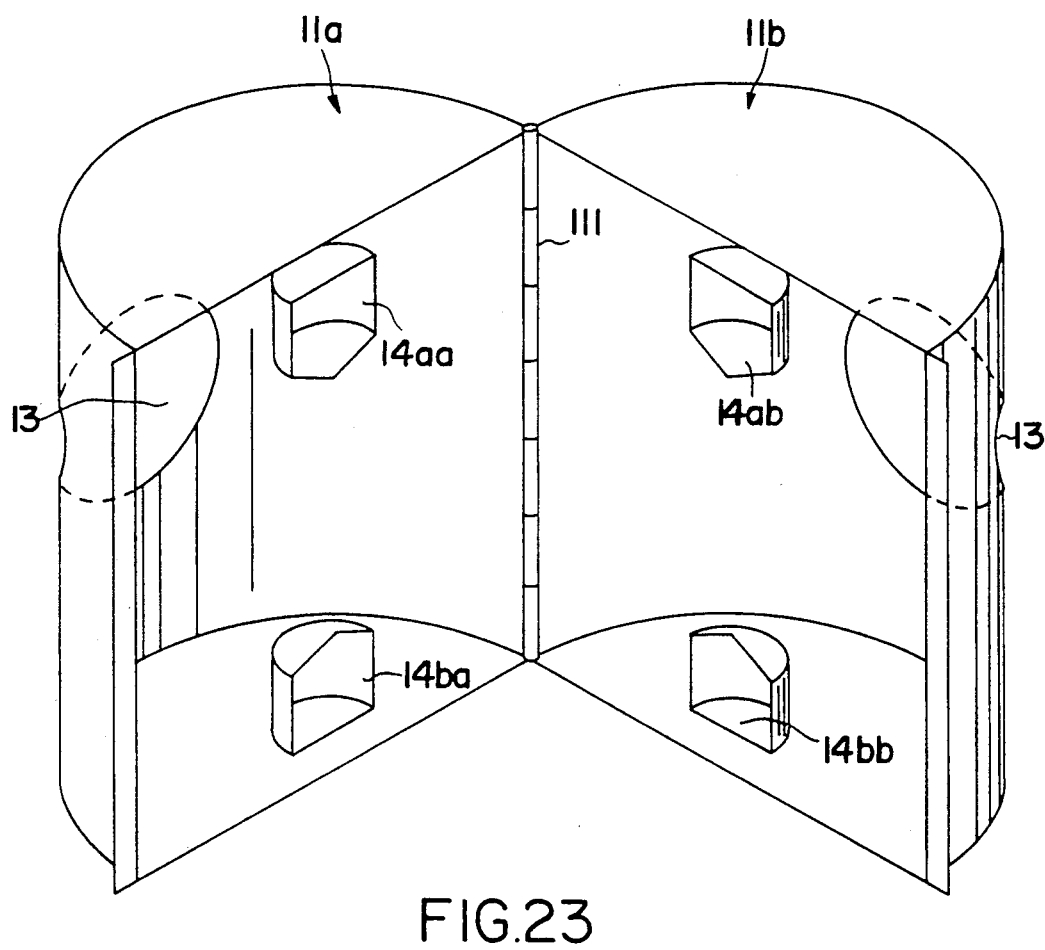
FIG. 23 is another embodiment of the cavity resonator.

The cavity resonator 11 of the above described embodiment consisted of a single body, but may also be divided by vertical parting lines into a pair of semi-cylindrical parts 11a and 11b which are joined by a connecting part (hinge) 111 so that one of them may be opened and closed with respect to the other as illustrated in FIG. 23. In this case, if necessary, the electric field concentrators are also divided into two parts 14aa and 14ab, and 14ba and 14bb.

According to this structure, it is possible to place a large living body or a large object into the cavity resonator not only through the opening 13 but also by opening the semi-cylindrical parts 11a and 11b without any difficulty. When the cavity resonator is to be divided, it should be divided by a vertical parting line because of the consideration not to obstruct electric current which flows vertically along the wall surface 16 inside the cavity resonator. In this case, the change in the resonant frequency may be minimized even when the connection by the connecting piece may be insufficient. Also, the loss is minimized. In short, according to this embodiment, a large living body or a large object can be easily accommodated in the cavity resonator without increasing a loss or affecting the resonant frequency.

Figure 24:
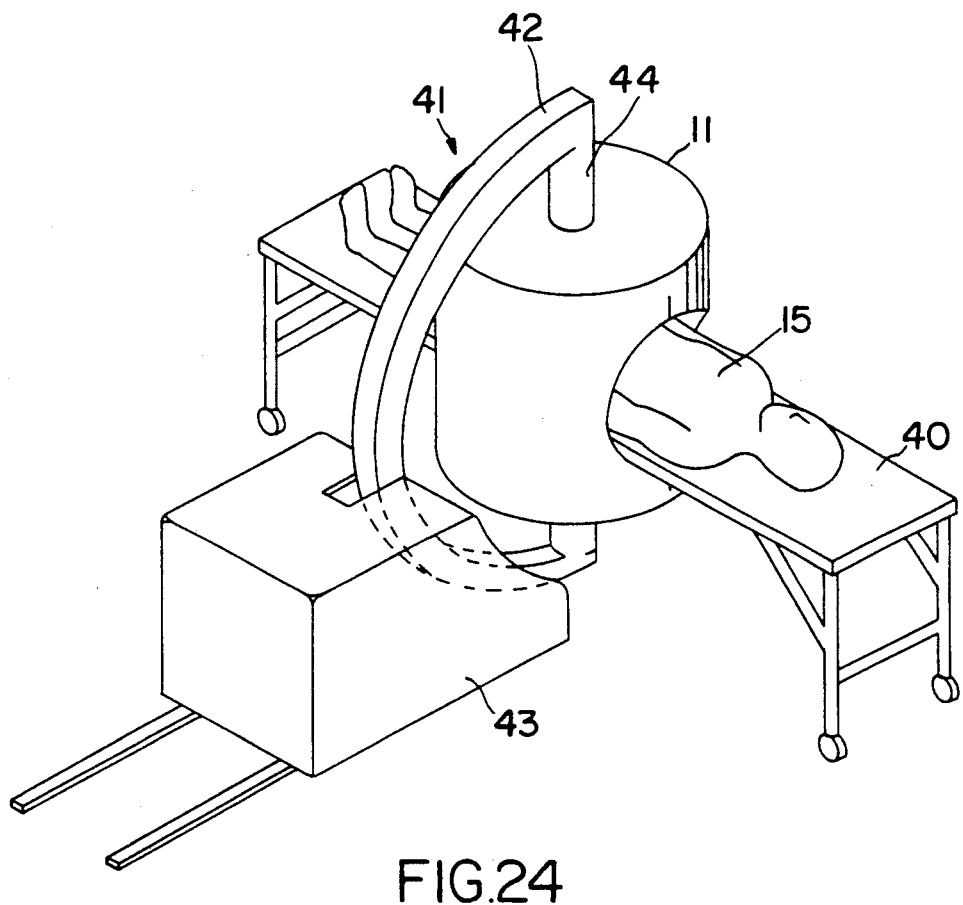
FIG. 24 is an overall system view of the electromagnetic heating device given as yet another embodiment of the present invention.

The electromagnetic heating device illustrated in FIG. 24 comprises a table 40 for securely supporting a living body 15, and a mechanism 41 which supports a cavity resonator 11 in a rotatable fashion relative to the table 40. The cavity resonator 11 itself may consist of the one illustrated in FIG. 1(B). The rotating mechanism 41 consists of a C arm 42 carrying the cavity resonator 11 by way of support rods 44 at its both ends, and a drive unit 43 for rotating this C arm 42.

According to this embodiment, when the cavity resonator 11 is rotated relative to the base 40 carrying the living body 15, the distribution of electric current on the surface of the living body 15 varies depending on the angle of the cavity resonator 11, but electric current is always supplied to cancerous tissues in the center of the living body to effectively heat them. Therefore, a concentrated heating effect can be obtained without excessively heating the surface, and a significant advantage can be gained in the field of cancer treatment.

Figure 25:
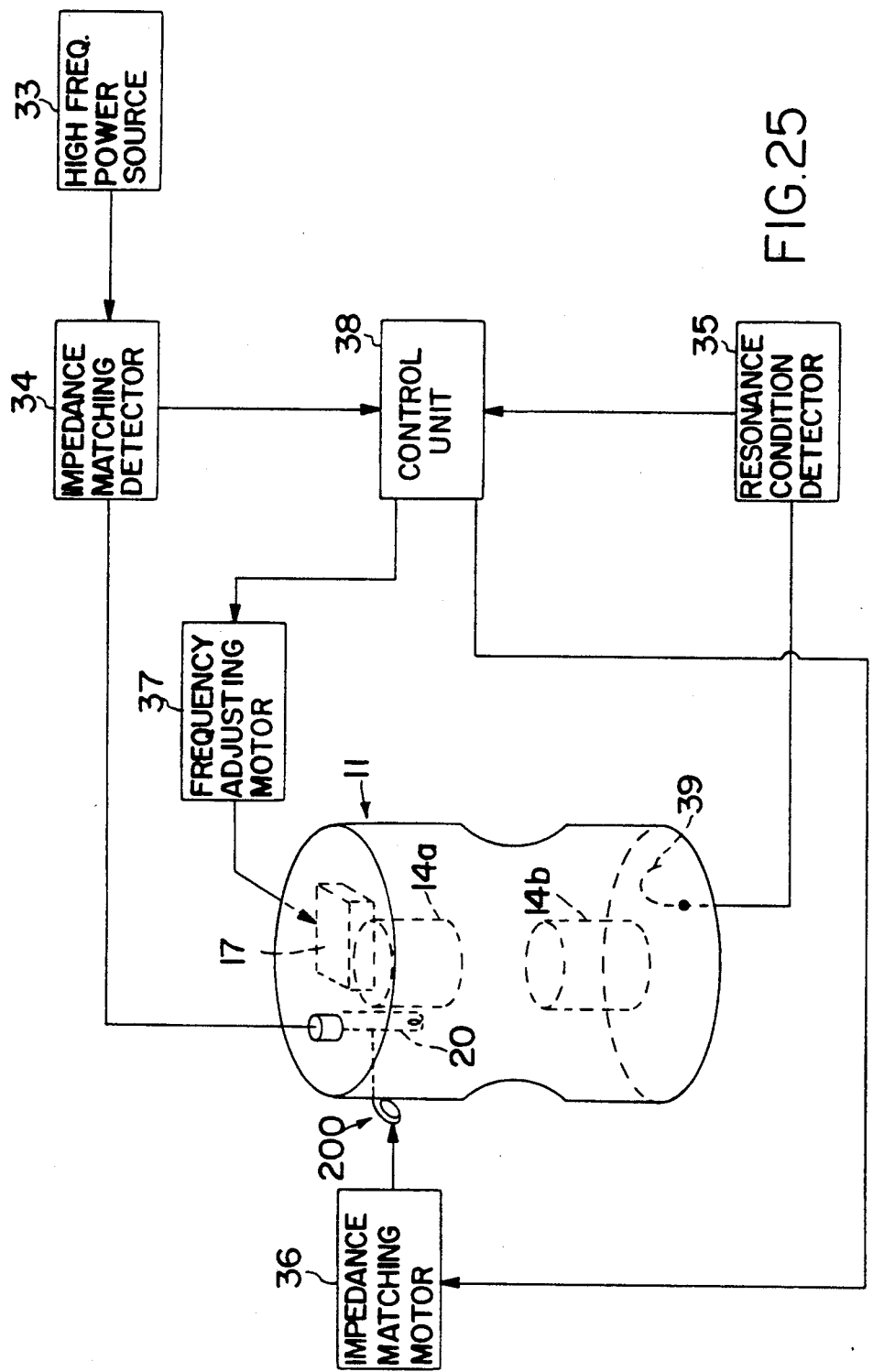
FIG. 25 is a block diagram of yet another embodiment of the electromagnetic heating device according to the present invention.

FIG. 25 is a block diagram of yet another embodiment of the electromagnetic heating device. This electromagnetic heating device comprises a high frequency power source unit 33, a cavity resonator 11, a impedance matching condition detector 34, a resonant condition detector 35, a impedance matching condition adjusting motor 36, a frequency adjusting motor 37, and a control unit 38 which controls the impedance matching adjusting motor 36 according to the impedance matching condition detected by the impedance matching condition detector 34 and the frequency adjusting motor 37 according to the resonant condition detected by the resonant condition detector 35.

The cavity resonator 11 incorporates therein a pair of electric field concentrators 14a and 14b, a frequency adjustor 17, a link coil 20, and a position varying unit 200 adjusting the position of the link coil 20 relative to the electric field concentrator 14a (refer to FIG. 6) which is given here as an example of the impedance matching unit, as well as a link coil 39 for detecting a resonant condition.

According to this embodiment, high frequency energy is supplied from the high frequency power source 33 to the cavity resonator 11. The impedance matching condition between the link coil 20 of the cavity resonator 11 and the high frequency power source unit 33 is detected by the impedance matching condition detector 34, and the control unit 38 automatically adjusts the impedance matching condition adjusting motor 36 according to the detected impedance matching condition so as to achieve an optimum impedance matching condition. If necessary, a voltage in the cavity resonator 11 may be obtained by the link coil 39 as a measurement sample for the resonant condition detector 35, and the control unit 38 controls the frequency adjusting motor 37 and finely adjusts the frequency adjustor 17 so as to match the resonant frequency of the cavity resonator 11 with the frequency of the high frequency power source unit 33 and obtain a maximum detected output.

If the resonant frequency of the cavity resonator is automatically matched with the frequency of the high frequency power source unit, high frequency electric power is always effectively injected. Further, a perfect impedance matching condition can be automatically attained between the link coil of the cavity resonator and the high frequency power source unit, and this also contributes to an effective injection of high frequency energy.

In the above described embodiments, the electric field concentrators were electrically out of contact with the frequency adjustor, but the present invention is not limited to these embodiments but is applicable to an embodiment integrally combining a frequency adjustor and an electric field concentrator. Further, instead of adjusting the frequency of the cavity resonator, it is possible to adjust the frequency of the high frequency power source with manual or other means as well know to persons skilled in the art.

Figure 26:
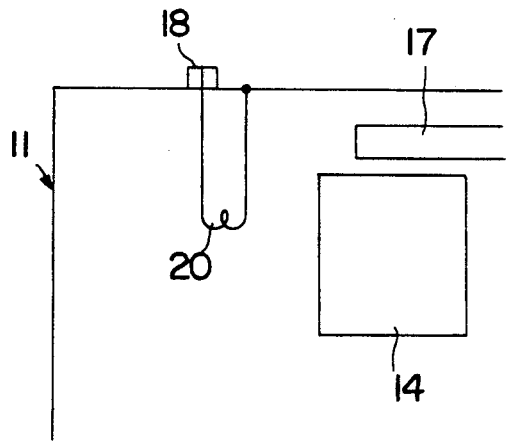
FIGS. 26 through 29 are drawings illustrating different embodiments of the high frequency energy supply circuit for the cavity resonator.

Referring to FIG. 26, it is possible to supply high frequency energy merely by connecting the link coil 20 to the connector 18, but connecting this link coil 20 to the connector 18 alone may not ensure an efficient transmission of high frequency energy due to mismatching of impedance between the link coil 20 and the feeder cable. Therefore, according to the present embodiment illustrated in FIG. 27, the variable capacitor 19 is connected between the connector 18 and the link coil 20 as a matching unit. According to this embodiment, the variable capacitor 19 is disposed externally of the upper wall of the cavity resonator 11, but it may also be placed internally of the upper wall of the cavity resonator 11.

Figure 27:
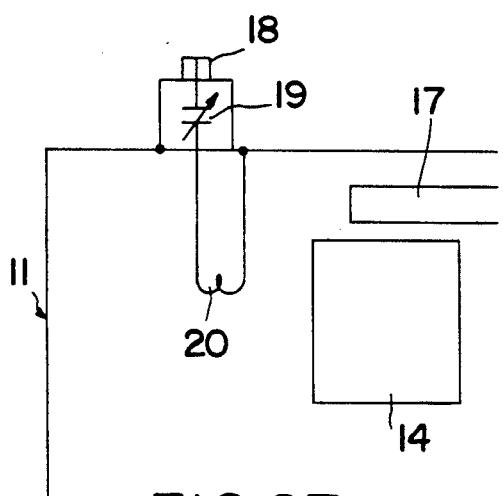

According to the matching circuits illustrated in FIGS. 1 and 27, by adjusting the variable capacitor 19, the resonant frequency of the link coil 20 is varied so as to coincide with the resonant frequency of the cavity resonator 11. When the impedance of the circuit consisting of the link coil 20 and the variable capacitor 19 coincides with that of the feeder cable, high frequency energy is most efficiently supplied to the cavity resonator 11.

Figure 28:
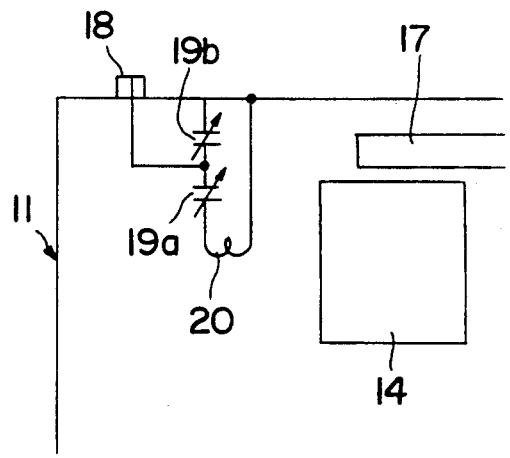
Figure 29:
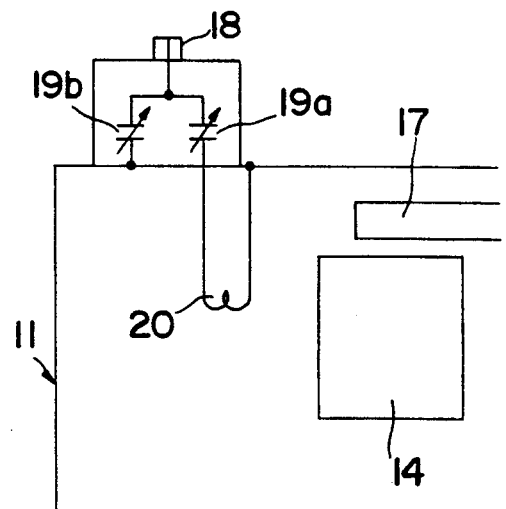

When the impedance of the link coil 20 does not coincide with that of the feeder cable, a pair of variable capacitors 19a and 19b may be utilized to match the resonant frequency of the link coil 20 and divide the impedance into a value which matches with the impedance of the feeder cable as shown in FIGS. 28 and 29. If the variable capacitors 19, 19a and 19b are placed remote from the link coil 20, since the cable extending therebetween is in a condition of impedance mismatch, flow of high frequency current is disturbed and heat is generated thereby with the result that the high frequency electromagnetic energy is not efficiently transmitted to the cavity resonator 11. To prevent this from occurring, the variable capacitors 19, 19a and 19b are placed adjacent to the link coil 20.

According to the electromagnetic heating device of these embodiments, high frequency energy can be efficiently supplied to the cavity resonator since the resonant condition of the link coil for supplying high frequency energy to the cavity resonator can be achieved and the impedance thereof can be matched with that of the feeder cable by the use of a variable capacitor. As a result, the living body of the object placed in the cavity resonator can be effectively heated.

Figure 30:
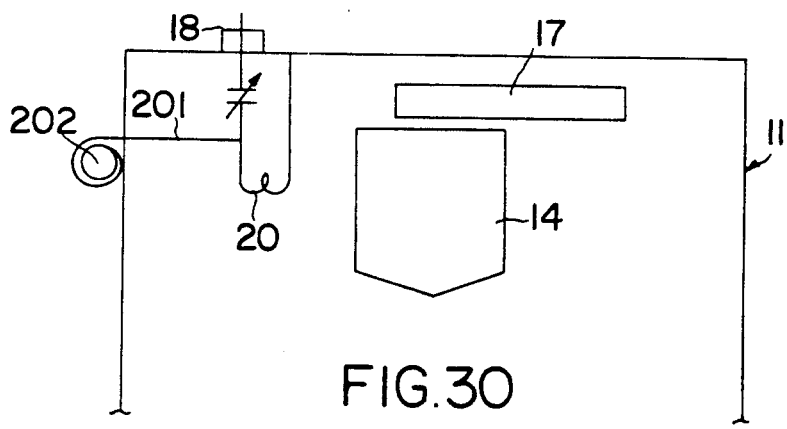
FIGS. 30 through 32 are drawings showing different modes of achieving a matching between a feeder cable and a link coil.

FIG. 30 shows a cavity resonator 11 for the electromagnetic heating device in which a length of non-conductive wire 201 is attached to the link coil 20, and the other end of the wire is wound or paid out by a pulley or a motor 202 from outside the cavity resonator 11 so that the distance between the link coil 20 and the electric field concentrator 14 may be adjusted. This is also applicable to the case in which only a link coil 20 is used as is the case with the embodiment illustrated in FIG. 26, and the impedance of the link coil 20 does not match with that of the feeder cable.

By moving the link coil 20 towards and away from the electric field concentrator 14, the impedance of the link coil 20 is modified. If the link coil 20 is brought closer to and further away from the electric field concentrator 14, the impedance of the link coil 20 diminishes and increases, respectively. Therefore, by moving the link coil 20 a suitable distance away from the electric field concentrator 14, it is possible to achieve an impedance matching between the link coil 20 and the electric field concentrator 14.

Figure 31:
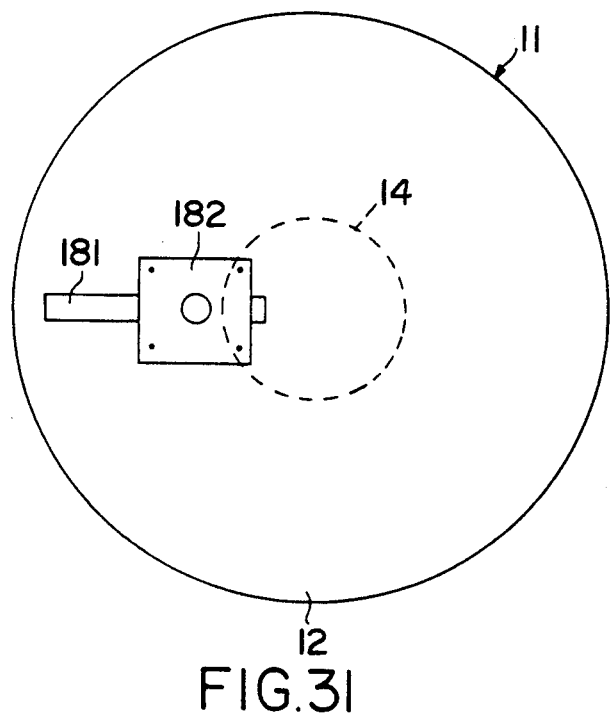

FIG. 31 shows another embodiment in which the distance between the link coil 20 and the electric field concentrator 14 is made variable. According to this embodiment, a connector 18, a variable capacitor 19 and a link coil 20 are incorporated in a mount 182 which is made moveable along a slot 181 provided in a bottom wall 12 of the cavity resonator 11.

Figure 32:
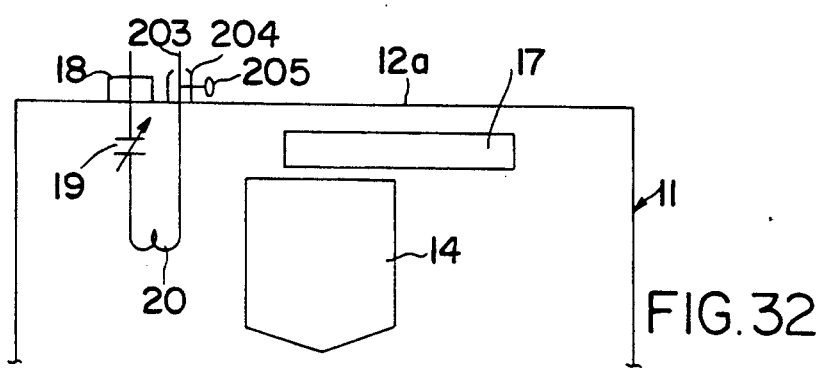

FIG. 32 shows another embodiment for achieving an impedance matching. A free end 203 of a link coil 20 is allowed to be moved into and out of a cavity resonator 11 from its upper end wall 12a, and a part of the free end 203 of the link coil 20 may be fixedly secured by a clamp member 204 and a fixing screw 205.

By varying the length of the link coil 20, the resonant frequency and the impedance of the link coil 20 can be changed. The shorter the link coil 20 is, the higher the resonant frequency becomes and the lower the impedance becomes. Thus, in combination with the use of a variable capacitor 19, it is possible to achieve resonant condition and impedance matching.

According to this embodiment also, since the resonant condition of the link coil for supplying high frequency energy to the cavity resonator can be attained, and the impedance of the link coil can be matched with that of the feeder cable, high frequency energy can be effectively supplied to the cavity resonator. As a result, a living body or an object placed in the cavity resonator can be effectively heated.

According to the electromagnetic heating device of the present invention, a strong current may be concentrated in the part of be heated, and the thermal action of the electric current heats this part to a high temperature. Therefore, the temperature rise in parts having a small electric current concentration is minimized, and a highly concentrated heating is made possible. Further, since the electric field concentrator and the cavity resonator are electrically out of contact with each other, it is possible to interpose a frequency adjustor therebetween, and allow the resonant frequency of the cavity resonator to be adjustable.

Since there are provided an electric field concentrator which is electrically out of contact with the cavity resonator, and a frequency adjusting means, when a living body is placed in the cavity resonator and the resonant frequency of the cavity resonator is affected by the size of the living body, it can be adjusted to a fixed value by using the frequency adjusting means. Therefore, the frequency of the high frequency power source unit may be fixed, and it becomes possible to achieve a drastic reduction in the overall cost of the heating device and to diminish interferences to radio communications.

According to the embodiment illustrated in FIG. 25, since an optimum impedance matching condition can be automatically achieved by the use of the link coil for detecting a signal in the cavity resonator, the resonance detector for picking up the signal from the link coil, and the control unit which controls the frequency adjusting means according to the resonance output, it is possible to achieve an optimum resonant condition and an optimum heating condition by adjusting the frequency adjusting means even when the frequency changes due to the change in the size or the position of the living body or the object so as to offer an effective electromagnetic heating device.

According to the invention, since the matching unit is provided adjacent to the link coil inside or outside of the cavity resonator, high frequency energy can be transmitted at a high efficiency. Furthermore, since the matching unit can be provided adjacent to the link coil, there is very little energy loss in the path therebetween, and this also contributes to an efficient transmission of high frequency energy.

According to the embodiments of the present invention utilizing an impedance matching means, since an optimum impedance matching condition can be automatically achieved by the use of the control unit which controls the impedance matching condition adjusting means, no effort is required to obtain a matched condition of impedance, and supply of high frequency energy can be achieved in an optimum condition.

What I claim is:

1. An electromagnetic heating device for heating a living body or an object, comprising:
    a cavity resonator made of hollow electroconductive material having an opening formed therein for receiving a living body or an object and heating said living body or object by a high frequency electromagnetic field produced therein, said cavity resonator having means for receiving high frequency energy; and
    an electric field concentrator disposed in said cavity resonator separately therefrom.

2. An electromagnetic heating device according to claim 1, wherein said electric field concentrator comprises a tubular body having a projection at a free end thereof.

3. An electromagnetic heating device according to claim 1, wherein said electric field concentrator comprises a pair of electric concentrating members spaced from each other to define a space for accommodating a living body or an object to be heated therebetween.

4. An electromagnetic heating device according to claim 1, further comprising frequency adjusting means for adjusting said high frequency electromagnetic field.

5. An electromagnetic heating device according to claim 4, wherein said frequency adjusting means comprises a variable capacitor connected between a wall portion of said cavity resonator and said electric field concentrator.

6. An electromagnetic heating device according to claim 4, wherein said frequency adjusting means comprises means for varying a position of said electric field concentrator relative to said cavity resonator.

7. An electromagnetic heating device according to claim 4, wherein said frequency adjusting means comprises means for deforming said electric field concentrator.

8. An electromagnetic heating device according to claim 4, wherein said frequency adjusting means comprises a variable inductance element connected between said electric field concentrator and a wall portion of said cavity resonator.

9. An electromagnetic heating device according to claim 4, wherein said frequency adjusting means comprises means for deforming said cavity resonator.

10. An electromagnetic heating device according to claim 4, wherein said frequency adjusting means comprises an enclosed container interposed between said electric field concentrator and a wall portion of said cavity resonator, and means for changing a kind of medium filled in said container.

11. An electromagnetic heating device according to claim 4, wherein said frequency adjusting means comprises an enclosed container interposed between said electric field concentrator and a wall portion of said cavity resonator, and means for changing a quantity of medium filled in said container.

12. An electromagnetic heating device according to claim 4, wherein said frequency adjusting means comprises an enclosed container interposed between said electric field concentrator and a wall portion of said cavity resonator and means for changing a volume of said container by changing a pressure of a medium filled in said container.

13. An electromagnetic heating device according to claim 10, 11 or 12, wherein said container is integral with said electric field concentrator.

14. An electromagnetic heating device according to claim 1, wherein said cavity resonator is divided into at least two parts by vertical parting lines so that said two parts may be opened and closed relative to each other.

15. An electromagnetic heating device according to claim 1, further comprising moveable support means for moving said cavity resonator with respect to a living body or an object to be heated.

16. An electromagnetic heating device for heating a living body or an object, comprising:
    a cavity resonator made of hollow electroconductive material having an opening formed therein for receiving a living body or an object and heating said living body or object by a high frequency electromagnetic field produced therein, said cavity resonator having means for receiving high frequency energy;
    a link coil connected to an input end of said cavity resonator; and
    impedance matching means provided adjacent to said link coil for adjusting impedance of the electromagnetic heating device.

17. An electromagnetic heating device according to claim 16, further comprising an electric field concentrator disposed in said cavity resonator separately therefrom.

18. An electromagnetic heating device according to claim 16, wherein said impedance matching means comprises a variable capacitor.

19. An electromagnetic heating device according to claim 16, wherein said impedance matching means comprises means for moving said link coil.

20. An electromagnetic heating device according to claim 16, wherein said impedance matching means comprises means for deforming said link coil.

* * * * *